United States Patent
Kirsch

(10) Patent No.: US 7,759,364 B2
(45) Date of Patent: Jul. 20, 2010

(54) METHOD FOR PRODUCING NON-HYDRATED FEXOFENADINE HYDROCHLORIDE AND A NOVEL CRYSTALLINE FORM OBTAINED THEREBY

(75) Inventor: Volker Kirsch, Schaffhausen (CH)

(73) Assignee: Cilag AG, Schaffhausen (CH)

( * ) Notice: Subject to any disclaimer, the term of this patent is extended or adjusted under 35 U.S.C. 154(b) by 825 days.

(21) Appl. No.: 10/468,964

(22) PCT Filed: Jan. 17, 2002

(86) PCT No.: PCT/CH02/00027

§ 371 (c)(1), (2), (4) Date: Mar. 24, 2005

(87) PCT Pub. No.: WO02/066429

PCT Pub. Date: Aug. 29, 2002

(65) Prior Publication Data

US 2005/0165056 A1 Jul. 28, 2005

(30) Foreign Application Priority Data

Feb. 23, 2001 (CH) ...................................... 329/01

(51) Int. Cl.
*A61K 31/445* (2006.01)
*C07D 211/34* (2006.01)

(52) U.S. Cl. ......................... 514/317; 546/238; 546/239

(58) Field of Classification Search .................. 514/317; 546/239, 238
See application file for complete search history.

(56) References Cited

U.S. PATENT DOCUMENTS

| 4,254,129 A | 3/1981 | Carr et al. | .................... 546/240 |
| 6,613,906 B1 * | 9/2003 | Davies et al. | ................ 546/239 |

FOREIGN PATENT DOCUMENTS

| WO | WO 95/31437 | 11/1995 |
| WO | WO 00/71124 | 11/2000 |
| WO | WO 01/94313 | 12/2001 |

OTHER PUBLICATIONS

Muzaffar et al. "Polymorphism and drug availability" J. Phar. 1(1) 59-66 (1979).*
Jain et al. "Polymorphisom in pharmacey" Indian Drugs 23(g)315-329 (1986).*
Doelker et al. "Crystalline modification . . . " CA 138:209993 (2002).*
Doelker et al. "Physicochemical behavior or active . . . " CA 132:325872 (2000).*
Otsuka et al. "effect of polymorphic . . . " Chem. Pharm. Bull, 47(6) 852-856 (1999).*
Taday et al. "Using terhertx pulse . . . " J. Pharm. Sci. v.92(4) p. 831-838(2003).*
Davidovich et al. "Detection of polymorphism . . . " Am. Pharm. Rev. vo. 7(1) p. 10, 12, 14,16,100 (2004).*
US pharmacopia, #23, National formulary #18, p. 1843-1844 (1995).*
Brittain "Polymorphism in pharmaceutical solids" p. 236 (1999).*
Berstein "polymorphism in molecular crystals" p. 115-118 (2002).*
Byrn et al. "solid state chemistry of drugs" p. 63 (1999).*
Martin-Luther University advanced practical lab course, p. 1-8 (from internet) (2007).*
J. Goerdeler: "Ammoniumverbindungen", Houben-Weyl, Methoden der Organischen Chemie, 4. Aufl., Band E16A (Teil2), Seite 1031 (1990), Georg Thieme Verlag, Stuttgart New York XP002193831 b) nichtquartäre Ammoniumsalze (Zeilen 7-9).
International Search Report issued in International Application No. PCT/CH02/00027 filed Jan. 17, 2002.

* cited by examiner

*Primary Examiner*—Celia Chang
(74) *Attorney, Agent, or Firm*—Hoffmann & Baron, LLP

(57) ABSTRACT

The invention relates to non-hydrated fexofenadine hydrochloride which can be obtained from a fexofenadine base and hydrogen chloride, according to the reaction conditions, either in the form of a novel polymorph ("form A"), in an amorphous form, or in the form of a mixture of different polymorphs. Said novel polymorph ("form A") can be used as a therapeutic active ingredient and can be processed to form a pharmaceutical containing the same and a pharmaceutically acceptable carrier. Said pharmaceutical is suitable for use as an antihistaminic agent, an antiallergic agent and/or a bronchodilating agent.

1 Claim, No Drawings

METHOD FOR PRODUCING NON-HYDRATED FEXOFENADINE HYDROCHLORIDE AND A NOVEL CRYSTALLINE FORM OBTAINED THEREBY

CROSS-REFERENCE TO RELATED APPLICATIONS

This application claims priority to PCT/CH02/00027, filed Jan. 17, 2002, which is incorporated herein by reference.

FIELD OF THE INVENTION

The present invention relates to non-hydrated fexofenadine hydrochloride.

BACKGROUND OF THE INVENTION

Fexofenadine hydrochloride (4-[1-hydroxy-4-[4-(hydroxydiphenylmethyl)-1-piperidinyl]butyl]-α,α-dimethylphenylacetic acid hydrochloride) has formula (I) below:

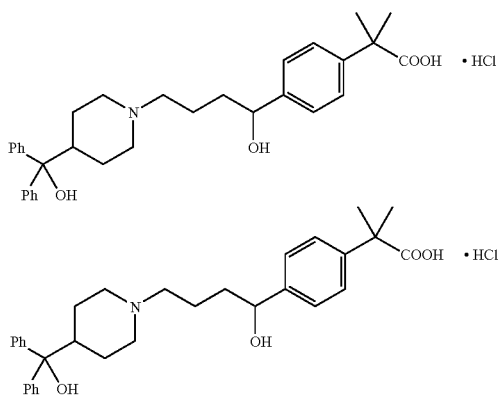

and is licensed by the US Food and Drug Administration (FDA) as an antihistamine, antiallergic and bronchodilator under the trade name Allegra®.

WO-A-95/31437 describes the preparation of hydrated polymorphs, or pseudo-morphs, of fexofenadine hydrochloride (form II and form IV) and their conversion to non-hydrated polymorphous forms (form I and form III) by azeotropic distillation or water-minimizing recrystallization.

WO-A-00/71124 describes amorphous, presumably non-hydrated fexofenadine hydrochloride and its preparation, a spray drying or freeze drying being carried out as the final stage.

SUMMARY OF THE INVENTION

It has now been found that non-hydrated fexofenadine hydrochloride can be prepared from fexofenadine base and hydrogen chloride in a simple and direct manner, without the need for operations such as azeotropic distillation, water-minimizing recrystallization, spray drying or freeze drying, to give the non-hydrated fexofenadine hydrochloride in the form of a novel polymorph ("form A") or in amorphous form or in the form of a mixture of different polymorphs, depending on the reaction conditions, wherein (a) fexofenadine base is suspended in a lower alkyl nitrile, a solution of hydrogen chloride in a lower alkanol, in a di(lower alkyl) ether or in a lower alkyl ester of a lower alkanecarboxylic acid is added, and the mixture is heated and then cooled, after which the non-hydrated fexofenadine hydrochloride is isolated in the form of the novel polymorph ("form A"), or (b) fexofenadine base is suspended in a lower alkane, in a di(lower alkyl) ether or in a lower alkyl ester of a lower alkanecarboxylic acid, a solution of hydrogen chloride in a lower alkanol, in a di(lower alkyl) ether or in a lower alkyl ester of a lower alkanecarboxylic acid is added, and the mixture is heated and then cooled, after which the non-hydrated fexofenadine hydrochloride is isolated in amorphous form, or (c) fexofenadine base is suspended in a lower alkyl nitrile, hydrogen chloride gas is passed into the suspension, and the mixture is heated and then cooled, after which the non-hydrated fexofenadine hydrochloride is isolated in the form of a mixture of different polymorphs.

DETAILED DESCRIPTION OF THE INVENTION

The compounds and radicals referred to above as "lower" appropriately contain up to eight carbon atoms. It is preferable to use acetonitrile as the lower alkyl nitrile, methanol as the lower alkanol, diethyl ether or diisopropyl ether as the di(lower alkyl) ether, ethyl acetate as the lower alkyl ester of a lower alkanecarboxylic acid, and n-hexane or n-heptane as the lower alkane.

Fexofenadine base (II) is obtainable in known manner from the hydrochloride of the corresponding keto ester, namely ethyl 4-[1-oxo-4-[4-(hydroxydiphenylmethyl)-1-piperidinyl]butyl]-α,α-dimethylphenylacetate (III).

The polymorph of fexofenadine hydrochloride obtainable according to variant (a) of the method according to the invention ("form A") has a melting range of 153 to 156° C. (DSC) and is characterized by the following XRD data (Table 1):

TABLE 1

XRD data of fexofenadine hydrochloride, form A (d = lattice spacing; the relative intensities were taken from the powder diagram obtained using CuK radiation.)

| d/Å | rel. intensity $(I/I_{max})/\%$ |
|---|---|
| 11.8 | 55 |
| 11.2 | 30 |
| 7.5 | 50 |
| 6.6 | 30 |
| 5.9 | 20 |
| 5.6 | 70 |
| 5.4 | 20 |
| 4.9 | 65 |
| 4.7 | 100 |
| 4.6 | 35 |
| 4.4 | 40 |
| 4.3 | 100 |
| 4.1 | 40 |
| 4.0 | 30 |
| 3.4 | 40 |

This polymorph is novel and also forms a subject of the present invention. It can be used as a therapeutic active ingredient and processed to a drug containing the active ingredient and a pharmaceutically acceptable excipient. This drug is suitable as an antihistamine, antiallergic and/or bronchodilator.

Pharmaceutically acceptable excipients which can be used in the preparation of drugs are generally known and familiar to all those skilled in the art.

By virtue of their different bioavailabilities, rates of release and solubilities, different forms of a pharmaceutical active ingredient, such as novel polymorphs in particular, can be of great benefit to the patients in question since they may allow a lowering of the dosage and/or a lengthening of the dosage intervals, making it possible to reduce the costs of the medication.

The Examples which follow will illustrate the invention without in any way limiting its scope.

EXAMPLES

The XRD spectra were recorded on a Philips ADP1700 computer-controlled powder diffractometer system with automatic divergence slit and secondary monochromator (graphite). The $CuK_\alpha$ radiation ($\lambda$ ($CuK_{\alpha1}$)=0.15406 nm and $\lambda$ ($CuK_{\alpha2}$)=0.15444 nm) from a copper tube (40 kV, 30 mA) was used and the spectra were recorded with $\Delta(2\Theta N)=0.02$ for a counting time of 3 s in the range $1.5° \leq 2\Theta \leq 40°$.

The differential scanning calorimetry (DSC) measurements were made on a METTLER DSC 821$^e$ apparatus with a start temperature of 25° C., an end temperature of 250° C. and a heating rate of 10 K min$^{-1}$. Standard aluminium crucibles with perforated lids were used as the sample vessels. The amount of sample was about 5 mg in each case.

Example 1

Synthesis of Fexofenadine Base 30 g of piperidine derivative III, 1.7 g of sodium borohydride and 7.4 g of sodium hydroxide were suspended in 200 g of ethanol and 44 g of water, refluxed for 3-5 h and then quenched with 10 g of acetone. The solvents were stripped off under vacuum and the residue was taken up in 200 g of water/acetone (2:1). The pH was adjusted to 5.8 to 6.0 by the addition of acetic acid, causing the fexofenadine base to crystallize out. The precipitate was filtered off, washed with water and dried under vacuum at 60° C. to give 22 g (83%) of product.

Example 2

Synthesis of Fexofenadine Hydrochloride, Form A 86 g of fexofenadine base were suspended in acetonitrile (700 g), and 30 g of a 20.6 percent solution of hydrogen chloride in diisopropyl ether were added at −10 to −12° C. The reaction mixture was heated at the reflux temperature for 1 h and then cooled. The hydrochloride was isolated by filtration, washed with acetonitrile and dried under vacuum at 100° C. to give 83 g (90%) of fexofenadine hydrochloride, form A.

Example 3

Synthesis of Fexofenadine Hydrochloride, Form A 10.0 g of fexofenadine base were suspended in acetonitrile (76 g), and 1.9 g of a 38.6 percent solution of hydrogen chloride in methanol were added at −10 to −12° C. The reaction mixture was heated at the reflux temperature for 1 h and then cooled. The hydrochloride was isolated by filtration, washed with acetonitrile and dried under vacuum at 100° C. to give 10.1 g (94%) of fexofenadine hydrochloride, form A.

Example 4

Synthesis of fexofenadine Hydrochloride, Form A 10.0 g of fexofenadine base were suspended in acetonitrile (76 g), and 3.7 g of a 19.5 percent solution of hydrogen chloride in ethyl acetate were added at −10 to −12° C. The reaction mixture was heated at the reflux temperature for 1 h and then cooled. The hydrochloride was isolated by filtration, washed with acetonitrile and dried under vacuum at 100° C. to give 9.8 g (91%) of fexofenadine hydrochloride, form A.

Example 5

Synthesis of Amorphous Fexofenadine Hydrochloride 10.0 g of fexofenadine base were suspended in n-heptane (90 g), and 4.02 g of a 17.9 percent solution of hydrogen chloride in diisopropyl ether were added at −10 to −12° C. The reaction mixture was heated at the reflux temperature for 1 h and then cooled. The hydrochloride was isolated by filtration, washed with n-heptane and dried under vacuum at 100° C. to give 9.7 g (90%) of amorphous fexofenadine hydrochloride.

Example 6

Synthesis of Amorphous Fexofenadine Hydrochloride 10.0 g of fexofenadine base were suspended in tert-butyl methyl ether (90 g), and 4.0 g of a 17.9 percent solution of hydrogen chloride in diisopropyl ether were added at −10 to −12° C. The reaction mixture was heated at the reflux temperature for 1 h and then cooled. The hydrochloride was isolated by filtration, washed with tert-butyl methyl ether and dried under vacuum at 100° C. to give 10.5 g (98%) of amorphous fexofenadine hydrochloride.

Example 7

Synthesis of Fexofenadine Hydrochloride in the Form of a Mixture of Different Polymorphs 5.1 g of fexofenadine base were suspended in acetonitrile (39 g). 0.4 g of hydrogen chloride was passed into the suspension at −10 to −12° C., after which the mixture was heated at the reflux temperature for 1.5 h and then cooled. The hydrochloride was isolated by filtration, washed with acetonitrile and dried under vacuum at 00° C. to give 5.1 g (92%) of fexofenadine hydrochloride in the form of a mixture of different polymorphs.

The invention claimed is:

1. A non-hydrated fexofenadine hydrochloride in the form of a novel polymorph ("form A"), wherein the novel polymorph has the following XRD data:

| D/Å | rel. intensity $(I/I_{max})/\%$ |
|---|---|
| 11.8 | 55 |
| 11.2 | 30 |
| 7.5 | 50 |

| D/Å | rel. intensity $(I/I_{max})/\%$ |
|---|---|
| 6.6 | 30 |
| 5.9 | 20 |
| 5.6 | 70 |
| 5.4 | 20 |
| 4.9 | 65 |
| 4.7 | 100 |
| 4.6 | 35 |
| 4.4 | 40 |
| 4.3 | 100 |

| D/Å | rel. intensity $(I/I_{max})/\%$ |
|---|---|
| 4.1 | 40 |
| 4.0 | 30 |
| 3.4 | 40 | and wherein the polymorph has a melting range of 153-156° C.

* * * * *